US011109538B2

(12) United States Patent
Chen et al.

(10) Patent No.: US 11,109,538 B2
(45) Date of Patent: Sep. 7, 2021

(54) METHOD FOR PRODUCING GALANTHAMINE BY A PLANT AND ELECTRICAL STIMULATION DEVICE

(71) Applicant: Industrial Technology Research Institute, Hsinchu (TW)

(72) Inventors: Wen-Yin Chen, Tainan (TW); Tsung-Lin Yang, Tainan (TW); Yung-Chi Kuo, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/858,040

(22) Filed: Dec. 29, 2017

(65) Prior Publication Data

US 2019/0203238 A1 Jul. 4, 2019

(51) Int. Cl.
*A01G 7/04* (2006.01)
*C12P 17/18* (2006.01)

(52) U.S. Cl.
CPC ............... *A01G 7/04* (2013.01); *C12P 17/18* (2013.01)

(58) Field of Classification Search
CPC .................................. A01G 7/04; C12P 17/18
See application file for complete search history.

(56) References Cited

U.S. PATENT DOCUMENTS

| | | | |
|---|---|---|---|
| 5,413,928 | A | 5/1995 | Weathers et al. |
| 6,319,919 | B1 | 11/2001 | Davis et al. |
| 7,851,448 | B2 | 12/2010 | Skubatch |
| 2010/0144003 | A1 | 6/2010 | Spragg et al. |
| 2010/0292466 | A1 | 11/2010 | Magnus et al. |

FOREIGN PATENT DOCUMENTS

| | | | | |
|---|---|---|---|---|
| CN | 1239504 | A | * 12/1999 | |
| CN | 1583749 | A | 2/2005 | |
| CN | 1239504 | C | 2/2006 | |
| CN | 101036627 | A | 9/2007 | |
| CN | 201861994 | U | 6/2011 | |
| CN | 102335297 | A | 2/2012 | |
| CN | 202285631 | U | 7/2012 | |
| CN | 103772403 | A | * 5/2014 | |
| CN | 103772403 | A | * 5/2014 | |
| JP | 3-285687 | A | 12/1991 | |
| KR | 10-1520477 | B1 | 5/2015 | |
| TW | I392496 | A | 5/2008 | |
| TW | 200845885 | A | 12/2008 | |
| WO | WO 2016053678 | | * 4/2016 | |
| WO | WO-2016053678 | A1 | * 4/2016 | ........... C07D 407/04 |

OTHER PUBLICATIONS

Poojary et al (Innovative Alternative Technologies to Extract Carotenoids from Microalgae and Seaweeds. Mar. Drugs, p. 1-34, Nov. 2016) (Year: 2016).*
Tallini et al (*Hippeastrum reticulatum* (Amaryllidaceae): Alkaloid Profiling, Biological Activities and Molecular Docking. Molecules, 1-14, Dec. 9, 2017). (Year: 2017).*
Bai et al (A High Yield Method of Extracting Alkaloid from Aconitum coreanum by Pulsed Electric Field. Chromatographia. 76:635-642, 2013) (Year: 2013).*
Poojary et al (Innovative Alternative Technologies to Extract Carotenoids from Microalgae and Seaweeds. Mar. Drugs, p. 1-34, Nov. 2016) (Year: 206).*
Martin et al (Acclimation kinetics of physiological and molecular responses of plants to multiple mechanical loadings. Journal of Experimental Botany, vol. 61, No. 9, pp. 2403-2412, 2010). (Year: 2010).*
Berkov et al (Plant Sources of Galanthamine: Phytochemical and Biotechnological Aspects. Biotechnol. & Biotechnol. 1170-1176, 2009) (Year: 2009).*
Tallini et al (*Hippeastrum reticulatum* (Amaryllidaceae): Alkaloid Profiling, Biological Activities and Molecular Docking. Molecules 2017, 1-14, Dec. 9, 2017). (Year: 2017).*
Jaeschke et al (Carotenoid and lipid extraction from Heterochlorella luteoviridis using moderate electric field and ethanol. Process Biochemistry 51. 1636-1643, 2016) (Year: 2016).*
Machado et al (Moderate electric fields can inactivate *Escherichia coli* at room temperature. Journal of Food Engineering 96. 520-527, 2010). (Year: 2010).*
Schranzhofer et al (Electrochemical impedance spectroscopy study of the SEI formation on graphite and metal electrodes. Journal of Power Sources. 153: 391-395, 2006). (Year: 2006).*
Ratnadewi (Alkaloids in Plant Cell Cultures. Intech, 1-23, Jul. 2017) (Year: 2017).*
Pu et al., "Iontophoretic Release and Transport of Alkaloids from Catharanthus Roseus Cells in a Ceramic Hollow Fiber Reactor", Biotechnology Letters, vol. 11, No. 2, 1989, pp. 83-86 (4 pages).
Taiwanese Office Action and Search Report, dated Nov. 28, 2018, for Taiwanese Application No. 106146486.
Xiayu et al., "Microwave Extraction Technique of Galanthamine in Lycoris", Chinese Agricultural Science Bulletin, vol. 32, No. 16, 2016, pp. 161-165 (5 pages), with abstract.
Yumin et al., "Progess in the Release of Plant Cell Intracellular Products", vol. 18, No. 1, 1998, pp. 17-21 (5 pages), with abstract.
Taiwanese Office Action for Appl. No. 106146486 dated Aug. 30, 2018.
Berkov, S., et al, "Galanthamine biosynthesis in plant in vitro systems," Eng. Life. Sci., 2014, vol. 14, pp. 643-650.
Chu, G., et al, "Eletroporation for the efficient transfecton of mammalian cells with DNA," Nucleic Acids Research, 1987, vol. 15, No. 3, pp. 1311-1326.
Eichhorn, J., et al, "Biosynthesis of the Amaryllidaceae Alkaloid Galanthamine," Phytochemistry, 1998, vol. 49, No. 4, pp. 1037-1047.

(Continued)

*Primary Examiner* — Ashley K Buran
*Assistant Examiner* — Wayne Zhong
(74) *Attorney, Agent, or Firm* — Birch, Stewart, Kolasch & Birch, LLP (57) ABSTRACT

A method for producing galanthamine using a plant, includes (a) performing a thermal treatment on a living plant to induce accumulation of galanthamine therein, wherein the living plant is a plant belonging to the family Amaryllidaceae; and (b) placing the living plant in a medium and performing an electrical stimulation treatment on the living plant to release the galanthamine from the living plant to the medium.

23 Claims, 5 Drawing Sheets

(56) References Cited

OTHER PUBLICATIONS

Fan, H., et al., "Investigation of Thermodynamic Mechanism for Extraction of Active Constituents in Lycoris radiata and Rhizma Polygoni Cuspidati Using Microwave-assisted Extraction," Chemical Journal of Chinese Universities, 2006, vol. 27, No. 12, pp. 2271-2276.

Ivanov, I., et al, "Elicitation of galanthamine biosynthesis by Leucojum aestivum liquid shoot cultures," Journal of Plant Physiology, 2013, vol. 170, pp. 1122-1129.

Kim, S.I., et al, "Effect of osmotic pressure on paclitaxel production in suspension cell cultures of Taxus chinensis," Enzyme and Microbial Technology, 2001, vol. 28, pp. 202-209.

Li, X., et al., "Effect of direct-current electric field on the growth of submerged macrophyte Vallisneria natans," J. Lake Sci., 2016, vol. 28, No. 5, pp. 1023-1030.

Lu, S.B., et al, "Physiological and Biochemical Response of Artificial Wetland Plant under Electric Field," Journal of Anhui Agri. Sci., 2010, vol. 38, No. 32, pp. 18255-18257.

Neumann, E., et al, "Gene transfer into mouse lyoma cells by electroporation in high electric fields," The Embo Journal, 1982, vol. 1, No. 7, pp. 841-845.

Saunders, J.A., et al, "Rapid Optimization of Electroporation Conditions for Plant Cells, Protoplasts, and Pollen," Molecular Biotechnology, 1995, vol. 3, pp. 181-190.

\* cited by examiner

METHOD FOR PRODUCING GALANTHAMINE BY A PLANT AND ELECTRICAL STIMULATION DEVICE

The technical field relates to a method for producing galanthamine (also called galantamine), and in particular, it relates to a method for producing galanthamine using a plant, and an electrical stimulation device suitable for this method.

TECHNICAL FIELD

The technical field relates to a method for producing galanthamine, and in particular, it relates to a method for producing galanthamine using a plant, and an electrical stimulation device suitable for this method.

BACKGROUND

Galanthamine hydrobromide was approved in 2001 by the US Food and Drug Administration (FDA) as one of the drugs that may be used for treatment of Alzheimer's disease and has now come onto the market in 22 countries. At present, the preparation methods of galantamine hydrobromide include full synthesis, semi-synthesis, and plant extraction.

Since the full synthesis method requires at least 8 steps and requires complicated purification methods, it is hard to reduce the cost of synthesis. Semi-synthesis is currently the main method of supplying galantamine hydrobromide, but its semi-synthesized precursors also have to come from plants belonging to the family Narcissusaceae and the family Amaryllidaceae. In terms of plant extraction, for example, a commodity material, Nivalin, is mainly derived from *narcissus*, however, the content of galanthamine (GAL) in *narcissus* is only about 0.01-0.1%, and that leads to high extraction costs in the back-end. Although other plants belonging to the genus *Lycoris* can also be sources for the raw materials for galanthamine, the low breeding number of seed balls and diseases have led to a reduction in the number of wild plants, and it is still not easy to reduce the cost of extraction.

Therefore, a novel and low-cost galantamine production method is still needed at present.

SUMMARY

The present disclosure provides a method for producing galanthamine using a plant, comprising: (a) performing a thermal treatment on a living plant to induce accumulation of galanthamine therein, wherein the living plant is a plant belonging to the family Amaryllidaceae; and (b) placing the living plant in a medium and performing an electrical stimulation treatment on the living plant to release the galanthamine from the living plant into the medium.

The present disclosure also provides an electrical stimulation device, comprising: a tank; a positive electrode; a negative electrode; and a potentiometric controller, wherein the positive electrode and the negative electrode are comb-electrodes, and the positive electrode and the negative electrode are disposed in an upright manner in the tank and are located on opposite sides, and the positive electrode and the negative electrode are connected to the potentiometric controller through respective wires.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 2B shows an actual photograph of an example of the electrical stimulation device 200;

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a method for producing galanthamine using a plant. The method for producing galanthamine using a plant of the present disclosure mentioned above may comprise the following steps, but it is not limited thereto.

First, a thermal treatment is performed on a living plant to induce accumulation of galanthamine therein, and the living plant may be a plant belonging to the family Amaryllidaceae.

The foregoing plant of Amaryllidaceae has no specific limitation, only if it is capable of producing galanthamine by metabolism, for example, the foregoing plant of Amaryllidaceae may comprise a plant belonging to the genus *Lycoris*, a plant belonging to the genus *Hippeastrum* or a plant belonging to the genus *Narcissus*, but it is not limited thereto. Examples for the plant belonging to the genus *Lycoris* may comprise, but are not limited to, *Lycoris aurea, Lycoris flavescens, Lycoris haywardii* and *Lycoris radiata* radiate. The plant belonging to the genus *Hippeastrum* may comprise *Hippeastrum equestre, Hippeastrum hybridum, Hippeastrum reginae, Hippeastrum brasiliense, Hippeastrum reticulatum*, etc., but it is not limited thereto. Moreover, examples for the plant belonging to the genus *Narcissus* may comprise *Narcissus tazetta, Narcissus jonquilla* and *Narcissus pseudonarcissus*, but they are not limited thereto. In one embodiment, in the method for producing galanthamine using a plant of the present disclosure, *Lycoris aurea* is used as the foregoing living plant."

Moreover, in the method for producing galanthamine using a plant of the present disclosure mentioned above, the thermal treatment performed on the living plant has no specific limitation, only if the temperature and/or processing time thereof do not result in damage or death to the living plant which is used. For example, the temperature of the thermal treatment mentioned above may be about 40-60° C., such as 40° C., 50° C., 55° C., 57° C., 60° C., but it is not limited thereto, and for example, time required for the thermal treatment mentioned above may be about 30-120 minutes, such as 40 minutes, 50 minutes, 60 minutes, 90 minutes, but it is also not limited thereto. In one embodiment, in the method for producing galanthamine using a plant of the present disclosure mentioned above, the temperature of the thermal treatment performed on the living plant may be about 55° C. Furthermore, in one embodiment, in the method for producing galanthamine using a plant of the present disclosure mentioned above, time required for the thermal treatment performed on the living plant may be about 60 minutes. In one specific embodiment, in the method for producing galanthamine using a plant of the present disclosure mentioned above, the thermal treatment is performed on the living plant at about 55° C. for about 60 minutes. In another specific embodiment, in the method for producing galanthamine using a plant of the present disclosure mentioned above, the thermal treatment is performed on the living plant at about 50° C. for about 90 minutes.

In addition, there are no particular limitations on the way in which the thermal treatment can be performed on the living plant, as long as the method used achieves the effect of heating the plants. For example, oven heating, double boiling, electric heating, or microwave heating can be adopted, but it is not limited thereto. In one embodiment, oven heating is used to perform the thermal treatment on the living plant. In another embodiment, double boiling is used to perform the thermal treatment on the living plant.

Moreover, in the method for producing galanthamine using a plant of the present disclosure, there is also no particular limitation on the part and/or ambit of the living plant subjected the thermal treatment, as long as the thermal treatment performed on this part and/or ambit is capable of promoting the production and/or accumulation of galanthamine. For example, the thermal treatment can be performed on the whole living plant or it can only be performed on a specific part or organ of the living plant, but it is not limited thereto. In one embodiment, the thermal treatment can be performed on the whole living plant. In another embodiment, the thermal treatment can be performed only on a bulb and a part below the bulb of the living plant.

In one specific embodiment, in the method for producing galanthamine using a plant of the present disclosure, placing the whole living plant in an oven to perform heating is used as the thermal treatment performed on the living plant mentioned above.

In one embodiment, in the step of performing the thermal treatment on the living plant mentioned above, the living plant is placed in a liquid. Since the liquid is mainly used to avoid and/or reduce the damage that may be caused to the living plant during the foregoing thermal treatment, if a liquid has the effects mentioned above, it can be used as a liquid adopted in the thermal treatment, and has no other particular limitation. Examples for the foregoing liquid may comprise, but are not limited to water, a medium.

In another embodiment, in the step of performing the thermal treatment on the living plant mentioned above, the thermal treatment can be performed on the living plant alone without the presence of liquid.

Next, after performing the thermal treatment on the living plant, the living plant is placed in a medium and an electrical stimulation is performed on the living plant to release the galanthamine from the living plant into the medium.

Since the medium mentioned above is mainly used to conduct electricity and used to avoid and/or reduce the damage that may be caused to the living plant during the foregoing electrical stimulation to achieve electrical stimulation to the living plant, if a liquid has the effects mentioned above, it can be used as a medium adopted in the method for producing galanthamine using a plant of the present disclosure, and has no other particular limitation.

In one embodiment, the content of nitrogen, phosphorous and potassium in the solid ingredients of the medium mentioned above may be about 30-55 w/w %, such as 30 w/w %, 35 w/w %, 40 w/w %, 42 w/w %, 45 w/w %, 50 w/w %, 55 w/w %, but it is not limited thereto.

Moreover, in one embodiment, the electrical conductivity of the medium mentioned above may be about 1500-2000 μS/cm, such as 1500-1800 μS/cm, 1650-2000 μS/cm, 1650-1800 μS/cm, but it is not limited thereto. In one specific embodiment, the electrical conductivity of the medium mentioned above may be about 1650-18000/cm.

Furthermore, the pH value of the medium mentioned above may depend on the pH value suitable for the growth of the Amaryllidaceae plant used, for example, the pH value of the medium mentioned may be in range of pH 5-7, such as pH 5-6, pH 5.5-6, pH 5.5-6.5, pH 5.8-6.5, pH 6-7, but it is not limited thereto. In one embodiment, the medium mentioned may have a pH value of about pH 5.8.

In addition, in the foregoing the embodiment in which the living plant is placed in a liquid in the step of performing the thermal treatment on the living plant, for a medium used as the liquid mentioned above, the ingredients thereof may be the same as or different from those of the medium used in the step of the electrical stimulation. In one embodiment, in the foregoing the embodiment in which the living plant is placed in a liquid in the step of performing the thermal treatment on the living plant, for a medium used as the liquid mentioned above, the ingredients thereof are the same as the medium used in the step of the electrical stimulation.

When the ingredients of the medium used in the thermal treatment step mentioned above are the same as those of the medium used in the step of electrical stimulation, after the thermal treatment step, the medium used in the thermal treatment step may be changed to a new medium and then the electrical stimulation is performed, or after the thermal treatment step, the medium used in the thermal treatment step may be directly used as the medium used in the follow-up electrical stimulation, i.e., after the thermal treatment step, the same medium is directly used to perform the electrical stimulation on the living plant without changing the medium. In one embodiment, after the thermal treatment step, the medium used in the thermal treatment step can be directly used as the medium used in the follow-up electrical stimulation.

The voltage applied in the above-mentioned electrical stimulation treatment is acceptable only if it causes no damage to the living plant. For example, a voltage applied by the electrical stimulation may be about 3-40 V, such as 3 V, 10 V, 15 V, 30 V, 35 V, 40 V, but it is not limited thereto. In one embodiment, the voltage applied by the electrical stimulation may be about 30 V.

Similarly, the time required for the above-mentioned electrical stimulation treatment is acceptable only if it causes no damage to the living plant, for example, it may be about 1-30 minutes, such as 2-10 minutes, 2-20 minutes, 5-10 minutes, 5-20 minutes, 5-30 minutes, but it is not limited thereto. In one embodiment, the time needed to perform the electrical stimulation treatment is 10 minutes. In another embodiment, the time needed to perform the electrical stimulation treatment is 20 minutes.

Furthermore, examples of the electrical stimulation treatment may include intermittent electrical stimulation, but they are not limited thereto. Power-on time for the intermittent electrical stimulation mentioned above may be 0.1-300 seconds, such as 0.1-30 seconds, 0.1-60 seconds, 0.1-120 seconds, 30-180 seconds, 60-300 seconds, but it is not limited thereto. Power-off time for the intermittent electrical stimulation mentioned above may be 0.1-300 seconds, such as 0.1-30 seconds, 0.1-60 seconds, 0.1-120 seconds, 30-180 seconds, 60-300 seconds, but it is not limited thereto. In one embodiment, the intermittent electrical stimulation mentioned above may be performed with a power-on time and a power-off time of both about 1 minute.

In the electrical stimulation treatment, a positive electrode and a negative electrode are in contact with the foregoing medium and are placed on both sides of the living plant and in contact with the living plant, or a positive electrode and a negative electrode are in contact with the foregoing medium and are placed on both sides of the living plant but are not in contact with the living plant, to perform the electrical stimulation on the living plant, but it is not limited thereto.

The electrical conductivities of the materials of the positive electrode and the negative electrode used in the electrical stimulation treatment may independently be greater than or equal to about 100 s/cm, such as about $1 \times 10^2$-$6 \times 10^5$ s/cm, but they are not limited thereto. Moreover, examples of the materials of the positive electrode and the negative electrode may independently include, but are not limited to, platinum, graphite, silver and gold. In one embodiment, the material used for both the positive electrode and the negative electrode is platinum.

Figure 1:
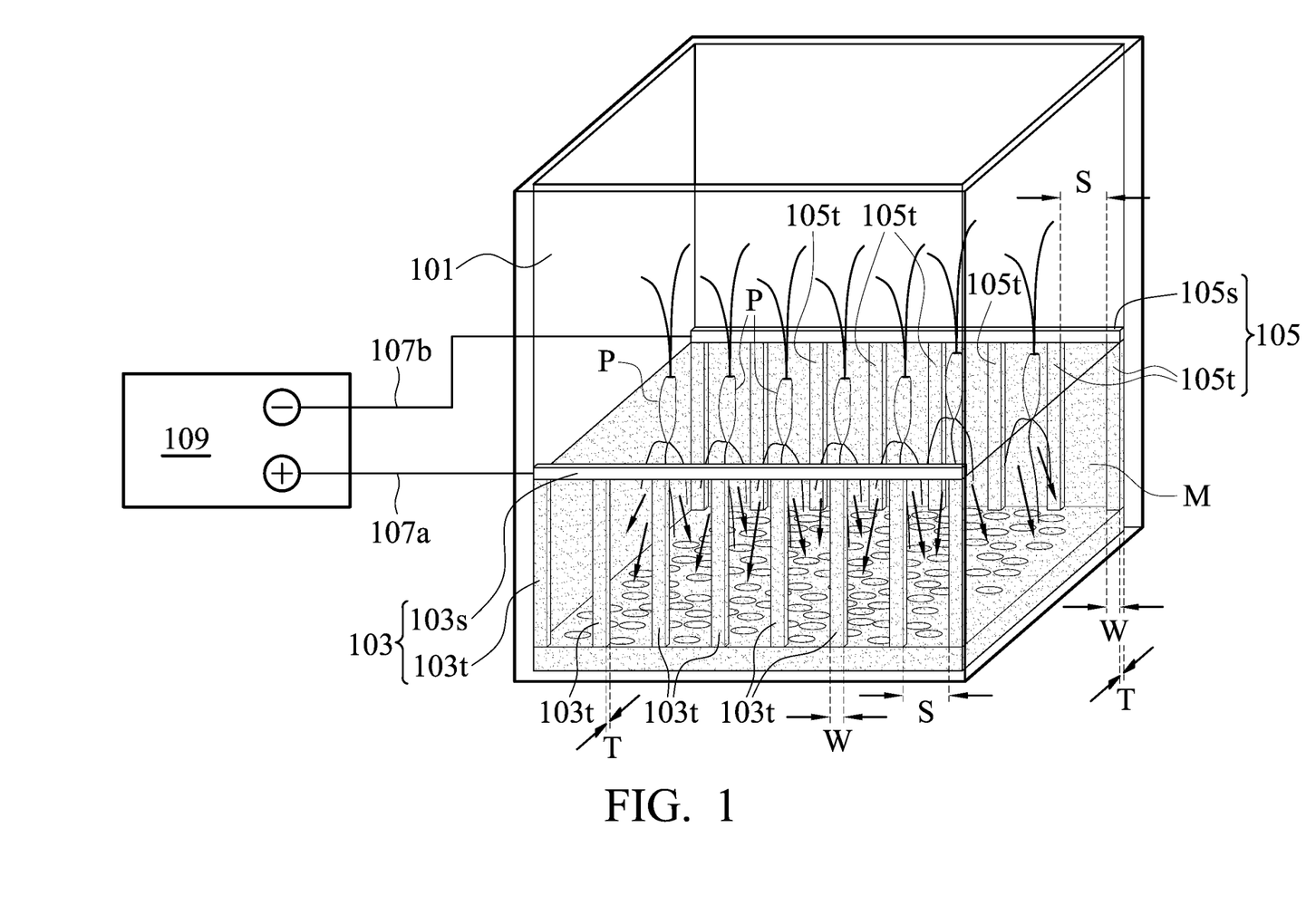
FIG. 1 shows a schematic diagram of an electrical stimulation device 100 which is adopted in one embodiment of the method for producing galanthamine using a plant of the present disclosure.

In one embodiment, the electrical stimulation treatment performed on the foregoing living plant may be performed by an electrical stimulation device shown in FIG. 1.

Refer to FIG. 1. FIG. 1 shows a schematic figure of an electrical stimulation device 100 which is adopted in one embodiment of the method for producing galanthamine using a plant of the present disclosure. The electrical stimulation device 100 has a tank 101, a positive electrode 103, a negative electrode 105, conductive wires 107a and 107b, and a potentiometric controller 109. The positive electrode 103 and the negative electrode 105 are comb-electrodes. Moreover, the positive electrode 103 and the negative electrode 105 are disposed in an upright manner in the tank 101 and are located on opposite sides.

Before performing the electrical stimulation, a medium M is added to the tank first, and at least one living plant P is placed in the medium in the tank. The positive electrode 103 is connected to the positive pole of the potentiometric controller 109 through the conductive wire 107a while the negative electrode 105 is connected to the negative pole of the potentiometric controller 109 through the conductive wire 107b, and a required voltage is set on the potentiometric controller 109. After that, the power of the potentiometric controller 109 is turned on to start the electrical stimulation treatment for the at least one living plant P.

The shape and size of the tank 101 have no particular limitation, and they can depend on the operation requirement, only if the tank is capable of accommodating the positive electrode 103, the negative electrode 105, the at least one living plant P and the medium M. For example, when the object to be treated is a small number of plants, the tank 101 may be a small tank which can accommodate the a small number of plants, such as 1-19 plants, and the positive electrode 103, the negative electrode 105 and the medium M, and when the object to be treated is a large number of plants, the tank 101 may be a large tank that can accommodate a large number of plants, such as tens, hundreds, or more plants, and the positive electrode 103, the negative electrode 105 and the medium M, but it is not limited thereto. In one embodiment, the tank is a rectangle shaped tank. The material of the tank 101 may be glass, plastic, etc., but it is not limited thereto.

The conductivity and material of the comb-shaped positive electrode 103 and negative electrode 105 may be same as those of the positive electrode and the negative electrode mentioned above, and therefore will not be described here.

In addition, the comb-shaped positive electrode 103 has a supporting portion 103s and at least two comb teeth 103t, wherein the comb teeth 103t are connected to the supporting portion 103s on the same plane and may be perpendicular to the supporting portion 103s, but it has no particular limitation. Similarly, the comb-shaped negative electrode 105 has a supporting portion 105s and at least two comb teeth 105t, wherein the comb teeth 105t are connected to the supporting portion 105s on the same plane and may be perpendicular to the supporting portion 105s, but it also has no particular limitation.

Since both the positive electrode 103 and the negative electrode 105 have the same appearance and structure, only the appearance and/or structure of the positive electrode 103 will be described below to avoid redundancy.

The number of comb teeth can be set depending on the operation requirements, and there is no particular limitation. For example, when the object to be treated is a small number of plants, the positive electrode 103 may have a smaller number of comb teeth, such as 2-10 comb teeth, and when the object to be treated is a large number of plants, the positive electrode 103 may have a greater number of comb teeth, such as 10-30 comb teeth, but is not limited thereto.

The size of the spacing S between two comb teeth of the comb-shaped positive electrode 103 is also not particularly limited, and may depend on the size of the tank and/or the width W and/or the thickness T of the comb teeth themselves. In one embodiment, the spacing S between the two comb teeth of the positive electrode 103 may be about 0.1-10 cm, but it is not limited thereto.

Similarly, the width W and/or the thickness T of the comb teeth 103t themselves are also not particularly limited, and may depend on the size of each spacing S for the comb teeth and/or the size of the tank.

Furthermore, in the case where the positive electrode 103 has more than 2 comb teeth, each spacing S for the comb teeth may be the same size, or may be different sizes. In one embodiment, each spacing S for the comb teeth may be the same size.

Figure 2:
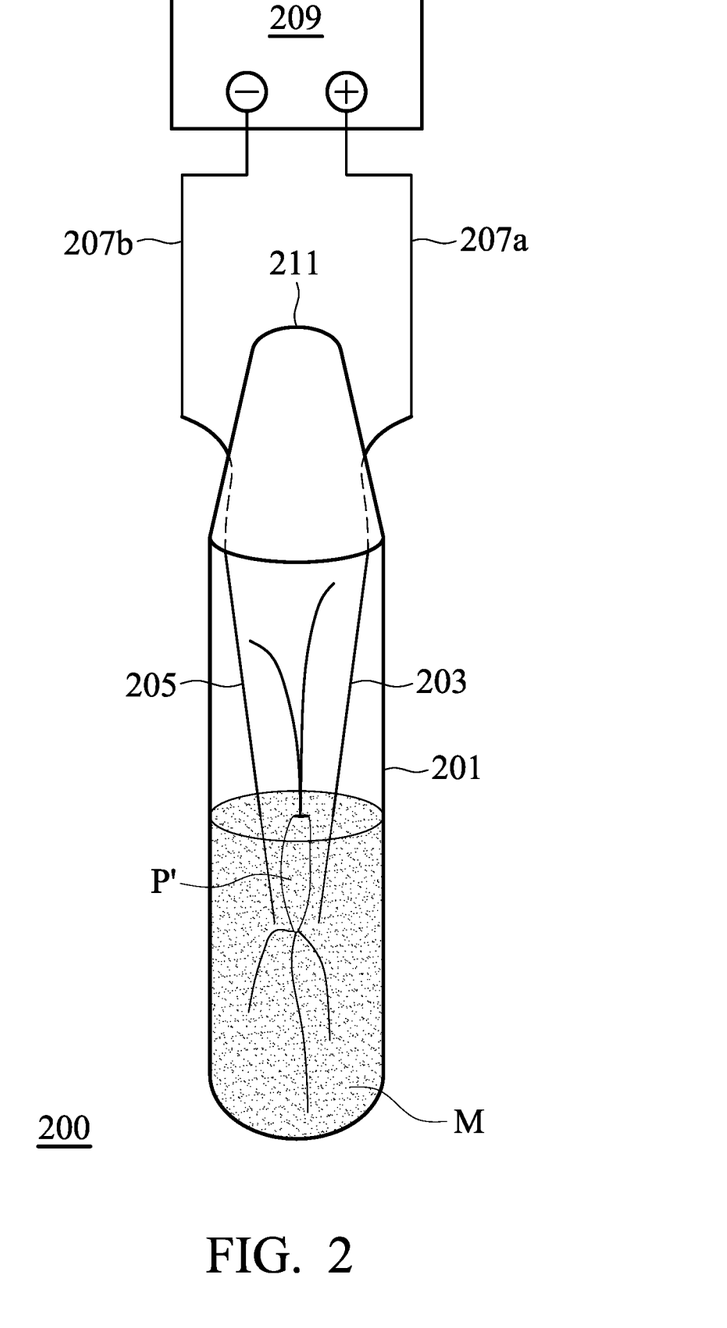
FIG. 2 shows a schematic diagram of an electrical stimulation device 200 which is adopted in another embodiment of the method for producing galanthamine using a plant of the present disclosure.

In another embodiment, the electrical stimulation treatment performed on the foregoing living plant may be performed by an electrical stimulation device shown in FIG. 2.

Refer to FIG. 2. FIG. 2 shows a schematic diagram of an electrical stimulation device 200 which is adopted in another embodiment of the method for producing galanthamine using a plant of the present disclosure. The electrical stimulation device 200 has a tube-shaped or column-shaped tank 201, a positive electrode 203, a negative electrode 205, conductive wires 207a and 207b, a potentiometric controller 209 and an upper cap 211, wherein the positive electrode 203 and negative electrode 205 pass through and extend from the upper cover 211, and when the upper cover 211 covers the opening of the tank 201, the positive electrode 203 and the negative electrode 205 enter the tank 201. Moreover, the positive electrode 203 and the negative electrode 205 are connected to the positive pole and the negative pole of the potentiometric controller 209 through the conductive wires 207a and 207b, respectively.

Before performing the electrical stimulation, the medium M mentioned above is added to the tank in advance, and a living plant P' is placed in the medium M in the tank. Next, the upper cap 211 is coved the opening of the tank 201 to let the positive electrode 203 and the negative electrode 205 enter the tank 201. Then, the positive electrode 203 is connected to the positive pole of the potentiometric controller 209 through the conductive wire 207a while the negative electrode 205 is connected to the negative pole of the potentiometric controller 209 through the conductive wire 207b, and a required voltage is set on the potentiometric controller 209. After that, the power of the potentiometric controller 209 is turned on to start the electrical stimulation treatment for at the living plant P'.

In one embodiment, the material of the tank 201 may be glass, plastic, etc., but it is not limited thereto.

The conductivity and material of the comb-shaped positive electrode 203 and negative electrode 205 may be same as those of the positive electrode and the negative electrode mentioned above, and therefore will not be described here.

The method for producing galanthamine using a plant of the present disclosure, in addition to the steps of the thermal treatment and the electrical stimulation mentioned above, can further comprise any step described below, or any combination thereof, as needed, but is not limited thereto.

First, the method for producing galanthamine using a plant of the present disclosure, before performing the thermal treatment on the living plant, may further comprises performing acclimation on the living plant.

Time required for the acclimation is not particularly limited as long as the above-mentioned living plant can be adapted to liquid culture. In one embodiment, time required for the acclimation may be about 0.5-14 days, such as 0.5 day, 1 day, 5 days, 7 days, 10 days, 14 days, but it is not limited thereto.

The acclimation mentioned above may comprise culturing the living plant in an acclimation medium, but it is not limited thereto. The ingredients of the acclimation medium mentioned above may be the same as or different from those of the medium used in the step of the thermal treatment (when in the step of performing the thermal treatment on the living plant, the living plant is placed in a medium). When the ingredients of the acclimation medium mentioned above are the same as those of the medium used in the step of the thermal treatment, after the step of acclimation, the medium used in the step of acclimation may be changed to a new medium and then the thermal treatment is performed, or after the step of acclimation, the medium used in the step of acclimation may be directly used as the medium used in the follow-up thermal treatment, i.e., after the step of acclimation, directly performing the thermal treatment on the living plant without a requirement of changing medium. In one embodiment, after the step of acclimation, the medium used in the step of acclimation can be directly used as the medium used in the follow-up thermal treatment.

Moreover, the method for producing galanthamine using a plant of the present disclosure, after placing the living plant in a medium and performing an electrical stimulation treatment on the living plant mentioned above, may further comprise a step of repairing the living plant.

The step of repairing the living plant may comprise placing the living plant in a repair medium, but it is not limited thereto. The ingredients of the repair medium mentioned above may be the same as or different from those of the medium used in the step of the electrical stimulation treatment. In one embodiment, the ingredients of the repair medium mentioned above may be the same as those of the medium used in the step of the electrical stimulation treatment. When the ingredients of the repair medium mentioned above are the same as those of the medium used in the step of the electrical stimulation treatment, after the electrical stimulation treatment, the living plant may be placed in a new medium to perform the repairing step, or after the electrical stimulation treatment, the medium used in the electrical stimulation treatment may be directly used as the medium used in the follow-up the repairing step, i.e., after the electrical stimulation treatment, directly performing the repairing on the plant in the same medium without a requirement of changing medium. In one embodiment, after the electrical stimulation treatment, the living plant is placed in a new medium to perform the repairing step.

The time for repairing the living plant mentioned above is not particularly limited as long as the living plant mentioned above can have sufficient time for repair. In one embodiment, time for repairing the living plant mentioned above may be about 2 hours-14 days, such as 2 hours, 4 hours, 8 hours, 16 hours, 0.5 day, 1 day, 5 days, 7 days, 10 days, 14 days, but it is not limited thereto.

Furthermore, the method for producing galanthamine using a plant of the present disclosure, after the step of repairing the living plant mentioned above, may further comprise sequentially repeating the step of performing a thermal treatment on the living plant, the step of placing the living plant in a medium and performing an electrical stimulation on the living plant, and the step of repairing the living plant mentioned above to be able to reuse an identical living plant multiple times.

In addition, the method for producing galanthamine using a plant of the present disclosure, after the step of placing the living plant in a medium and performing an electrical stimulation on the living plant mentioned above, may further comprise a step of collecting galanthamine from the foregoing medium.

The step of collecting galanthamine from the foregoing medium has no particular limitation, only if the product therefrom contains galanthamine, for example, any isolation and/or purification method may be used, but it is not limited thereto. In one embodiment, galanthamine is collected by performing lyophilization on the medium mentioned above.

In one embodiment, in the method for producing galanthamine using a plant of the present disclosure, first, a whole plant of a living plant of *Lycoris aurea* is heated by an oven to inducing accumulation of galanthamine therein, and then the a living plant of *Lycoris aurea* is placed in a medium with an electrical conductivity of about 1650-1800 μS/cm and subjected to an intermittent electrical stimulation at a voltage of 30 V for an interval of 1 minute (electrifying for 1 minute, stopping electrifying (power-off) for 1 minute) for a total of 20 minutes, and after that the medium mentioned above is collected and lyophilized to obtain galanthamine.

In the foregoing embodiment, before performing oven heating on the living plant of *Lycoris aurea*, the living plant of *Lycoris aurea* may be acclimatized for 7 days in advance.

By the method for producing galanthamine using a plant of the present disclosure, the desired galantamine can be repeatedly obtained without damaging the plants. In other words, by the method for producing galanthamine using a plant of the present disclosure, the plant itself can be used as a chemical factory for producing galantamine, and the phytochemical factory can continuously produce galantamine.

In addition, according to the above, the present disclosure also provides an electrical stimulation device, which can be any the electrical stimulation device 100 described above. The description of the electrical stimulation device 100 is the same as described above, and thus it is not repeated here.

EXAMPLES

A. Materials

1. Living Plants
1.1 *Lycoris aurea*
1.1.1 Whole Plant of *Lycoris aurea*
Source: Obtained from the tissue culture laboratory of the Industrial Technology Research Institute
1.2 *Hippeastrum equestre*
1.2.1 Whole Plant of *Hippeastrum equestre*
Source: Obtained from the tissue culture laboratory of the Industrial Technology Research Institute
2. Medium
2.1 Peters Professional 5-11-26 (Hydroponic Special)
2.1.1 Manufacture
Scotts (USA)
2.1.2 Preparation of Medium
5 g of the commercial medium powder was added to a serum bottle containing 1 L water (for preparing 200× diluted medium), and a stir bar was added to the serum bottle. The serum bottle was placed on a magnetic stirrer and stirring is performed to dissolve the powder to form a medium. After stirring for 20 minutes, the medium was adjusted to pH 5.8 by titration with alkaline potassium hydroxide (KOH), and this pH was more suitable for the growth of plants of Amaryllidaceae.

The electrical conductivity (EC) of the prepared medium was 1650-1800 μS/cm, and the content of the main ingredients of the solid composition for the medium, nitrogen, phosphorous and potassium, was about 42% (w/w).

Next, the prepared medium was high-strength autoclaved for 15 minutes. After that, the medium was cooled for ready to use.

2.2 MS Medium (Murashige and Skoog Medium)
2.2.1 Prepared Based on Ingredients and their Contents Specified by General MS Medium B. Configuration of Electrical Stimulation Device Used for Electrical Stimulation Treatment FIG. 2 shows a schematic diagram of the electrical stimulation device used in this experiment. Refer to FIG. 2.

First, an electrical stimulation device 200 is provided. The electrical stimulation device 200 had a glass tank (glass test tube) 201, a positive electrode of platinum wire 203, a negative electrode of platinum wire 205, conductive wires 207a and 207b, a potentiometric controller 209 and an upper cap 211, wherein the positive electrode 203 and negative electrode 205 pass through and extend from the upper cover 211, and when the upper cover 211 covers the opening of the tank 201, the positive electrode 203 and the negative electrode 205 enter the tank 201. Moreover, the positive electrode 203 and the negative electrode 205 are connected to the positive pole and the negative pole of the potentiometric controller 209 through the conductive wires 207a and 207b, respectively. Before the electrical stimulation treatment, the medium M prepared by the above "2.1.2" of "A. Materials" (electrical conductivity (EC) of the prepared medium was 1650-1800 μS/cm, pH 5.8) was added to the tank 201.

C. Test for Voltage Suitable for Electrical Stimulation of Living Plants

A whole plant of *Lycoris aurea* P' was placed in the electrical stimulation device 200 mentioned above, wherein the bulb and a part below the bulb of the *Lycoris aurea* P' were immersed in the medium mentioned above. Next, the upper cap 211 was covered on the opening of the glass tank (glass test tube) to keep the ends of the platinum electrodes close to both sides of the bulb of *Lycoris aurea* P'. After that, electrifying is started and the current change was monitored to confirm the voltage range of the electrical stimulation suitable for the living plant.

The results shows that when a low voltage of 4.1 V is applied, the plant, the medium, and the electrical stimulation device are conductive, and the current can be 0.01 ampere. When the voltage is adjusted to a high voltage of 30 V, the current value is only raised to 0.27 ampere. Accordingly, it is confirmed that the electrical stimulation treatment can be performed over a wide voltage range.

D. Examples and Comparative Examples

1. Example 1

Figure 3A:
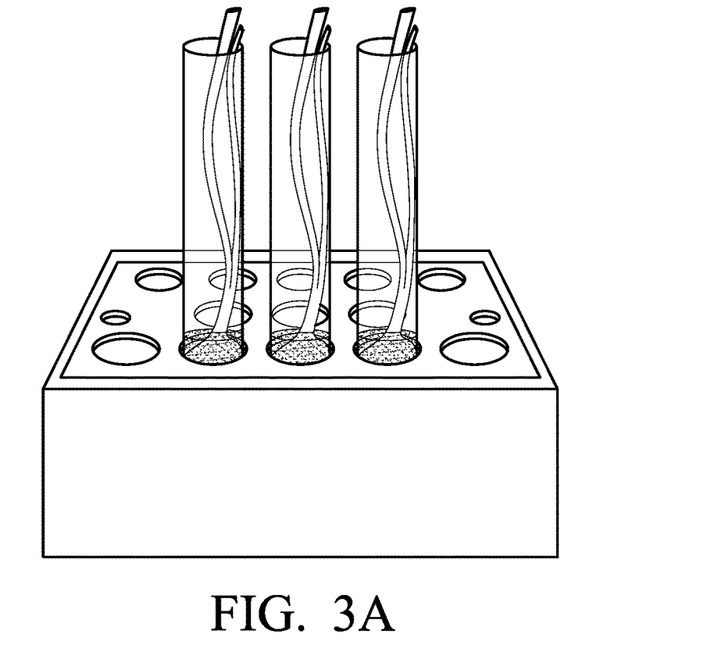
FIG. 3A shows one embodiment of the thermal treatment in the method of the present disclosure in which water bath heating is only performed on the bulb and a part below the bulb of the plant.

Determination of induction of galanthamine accumulation of plant by thermal treatment
Methods
1.1 Heating of Bulb and a Part Below the Bulb of Plant
A living plant of *Lycoris aurea* (source: tissue culture seedlings; culturing time: 6 months, spherical diameter of bulb: 0.8-1 cm) was placed in a glass test tube and RO water was added therein, wherein RO water only covered up to the bulbs. Next, the bulb and a part below the bulb of the plant were heated by a 50° C. water bath for 90 minutes (Heating range: water bath heating was only performed on the bulb and a part below the bulb) (refer to FIG. 3A). After the heating was completed, the plant was taken out, the whole plant was extracted, and a liquid chromatography-mass spectrometry (LCMS) analysis was performed on the whole plant extract to determine the galanthamine (GAL) content in the whole plant.

Figure 3B:
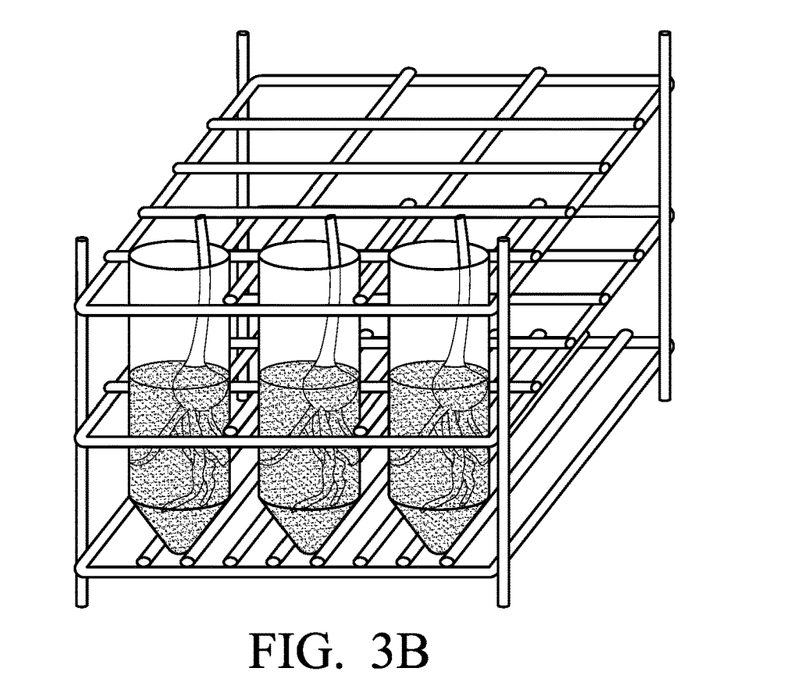
FIG. 3B shows one embodiment of the thermal treatment in the method of the present disclosure in which oven heating is performed on the whole plant.

1.2. Heating of Whole Plant of Plant
A living plant of *Lycoris aurea* (source: tissue culture seedlings; culturing time: 6 months, spherical diameter of bulb: 0.8-1 cm) was placed in a test tube and RO water was added therein, wherein RO water only covered up to the bulbs. Next, the test tube was placed in a 50° C. oven for 90 minutes (Heating range: the whole plant) (refer to FIG. 3B).

After the heating was completed, the plant was taken out, the whole plant was extracted, and a liquid chromatography-mass spectrometry analysis was performed on the whole plant extract to determine the galanthamine content in the whole plant.

Results

Figure 4:
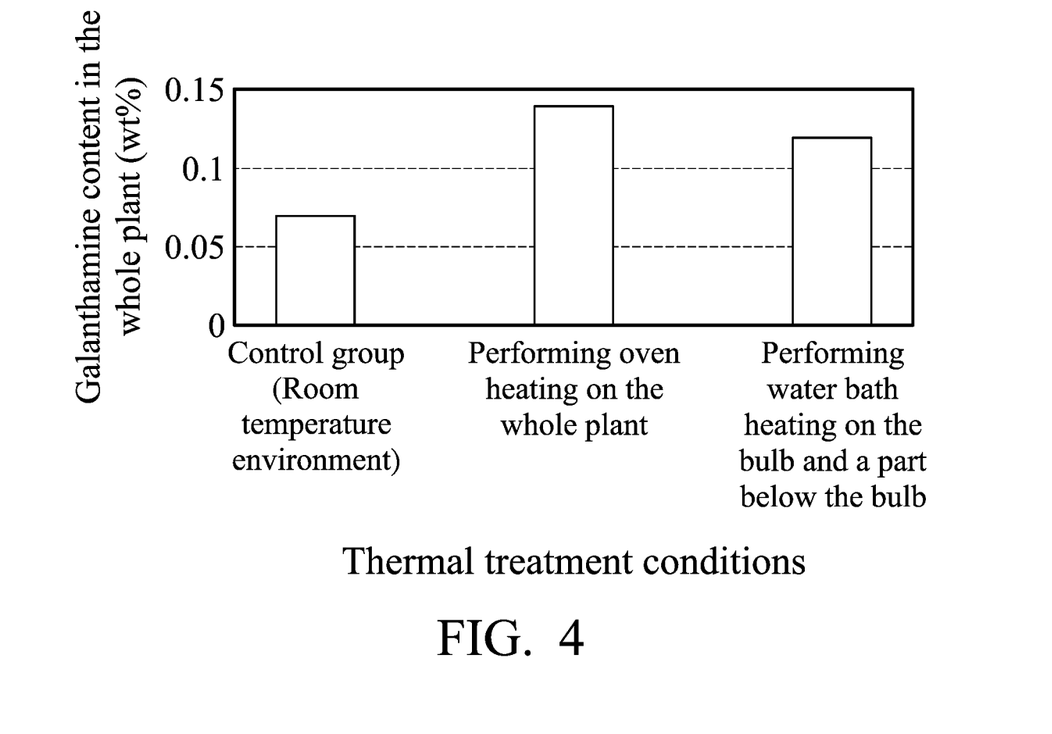
FIG. 4 shows the galanthamine contents of the plant of which the bulb and a part below the bulb are heated and the whole plant that is heated in one embodiment of the present disclosure.

The galanthamine contents of the plant of which the bulb and a part below the bulb were heated and the whole plant that was heated are shown in FIG. 4.

FIG. 4 shows that as compared to the control group (the plant is placed at room temperature without heating treatment), both the plant of which the bulb and a part below the bulb are heated and the whole plant that is heated have higher galanthamine content. The galanthamine content of the plant of which the bulb and a part below the bulb are heated and the whole plant that is heated are between 1.75-fold and 2-fold that of the control group.

Moreover, FIG. 4 also shows that the galanthamine content of the whole plant that is heated is higher than that of the plant of which the bulb and a part below the bulb are heated.

2. Example 2

Performing thermal treatment or combination of thermal treatment and electrical stimulation treatment on *Lycoris aurea*

Methods 2.1 Acclimation of Plant

The filter paper was cut and then placed at the bottom of a round glass test tube (diameter 3.5 cm) for supporting a plant. Next, a plant, *Lycoris aurea*, was placed in the test tube, and 30 mL of the medium prepared by the above "2.1.2" of "A. Materials" was added to the test tube. After that, the plant was cultured for performing acclimation of the plant. After 7 days of acclimation, experiments on the thermal treatment and electrical stimulation were performed on the plants.

2.2 Thermal Treatment

After the acclimation, the test tube containing the plant and the medium (the original medium was kept, and not changed to a new medium) was directly placed in a 55° C. oven for thermal treatment for 60 minutes. After that, the medium in the glass test tube was recovered in a 50 mL plastic centrifuge tube and frozen at −20° C. Next, the recovered medium was lyophilized to form a powder.

A liquid chromatography-mass spectrometry analysis was performed on the obtained powder to determine the content of galanthamine therein to investigate the effect of the thermal treatment only on a plant that produces galanthamine and that releases it into the medium.

2.3 Combination of Thermal Treatment and Electrical Stimulation Treatment

After the acclimation, the test tube containing the plant and the medium (the original medium was kept, and not changed to a new medium) was directly placed in a 55° C. oven for thermal treatment for 60 minutes. Two platinum wire respectively used as a positive electrode and a negative electrode were passed through an upper cap and fixed thereon. After the thermal treatment, the upper cap having the positive electrode and the negative electrode was covered on the opening of the test tube containing the plant and medium (the original medium was kept, and not changed to a new medium) to let the positive electrode and the negative electrode enter the test tube and close the upper cap and the opening. It was noted that the positive electrode and the negative electrode could not contact each other inside the test tube, and the ends of the two electrodes had to be placed on both sides of the bulb of the plant (refer to FIG. 2). After that, an intermittent electrical stimulation was performed on the plant, i.e. the plant was electrified in an intermittent way. Specifically, after 1 minute of electrifying, electrifying was stopped for 1 minute, and then the electrification and the interruption of the electrification mentioned above were repeated to avoid a violent rise in temperature due to the thermoelectric effect. After repeating the foregoing pattern of electrification 10 times, the medium in the glass test tube was recovered in a 50 mL plastic centrifuge tube and frozen at −20° C. After that, the recovered medium was lyophilized to form a powder.

A liquid chromatography-mass spectrometry analysis was performed on the obtained powder to determine the content of galanthamine therein to investigate the effect of the thermal treatment plus the electrical stimulation treatment on a plant that produces galanthamine and that releases it into the medium.

2.4 The plants subjected to the foregoing steps 2.2 and 2.3 were placed in test tubes and continuously cultured with new medium (the medium prepared by the above "2.1.2" of "A. Materials"), and after 7 days, the treatments of the steps 2.2 and 2.3 were respectively performed on the same plants to determine the galanthamine-release amounts for the plants mentioned above on Day 7 of the experiments.

2.5 The treatment of the step 2.4 was repeated to determine the galanthamine-release amounts for the plants mentioned above on Day 14 of the experiments.

Results

Figure 5:
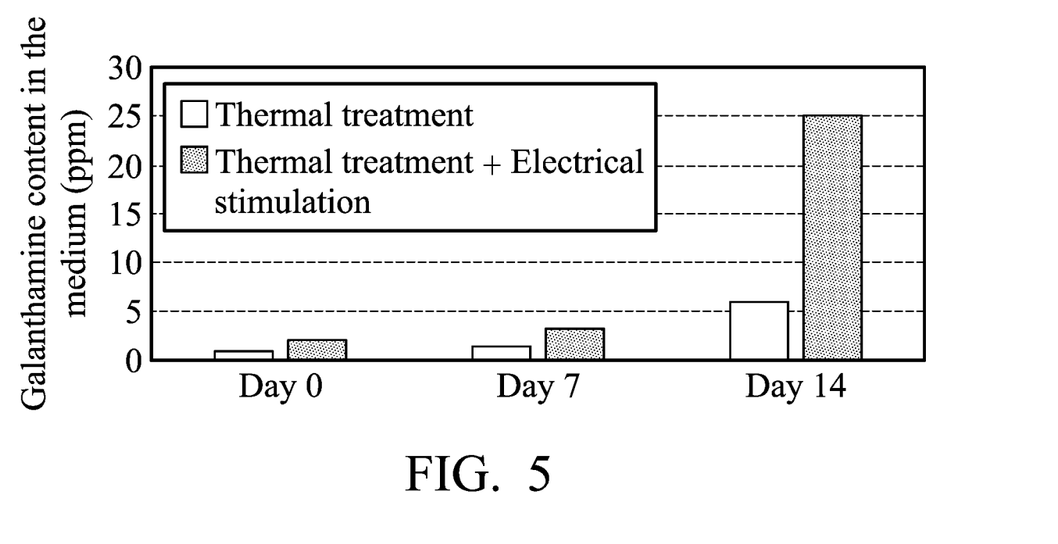
FIG. 5 shows the amounts of galanthamine released from the plant only subjected to the thermal treatment and the plant subjected to a combination of the thermal treatment and the electrical stimulation treatment in one embodiment of the present disclosure. Day 0: the day on which the acclimation is completed.

The amounts of galanthamine released into the medium from a plant that was only subjected to the thermal treatment and a plant that was subjected to a combination of the thermal treatment and the electrical stimulation treatment are shown in FIG. 5.

FIG. 5 shows that on Day 0, Day 7 and Day 14 of the experiments, the amounts of galanthamine released into the medium from the plants that were subjected to a combination of the thermal treatment and the electrical stimulation treatment are all greater than those of the plants that were only subjected to the thermal treatment.

3. Example 3

Performing combination of thermal treatment and electrical stimulation treatment on *Hippeastrum equestre*.

Methods 3.1 Acclimation of Plant

The filter paper was cut and then placed at the bottom of a round glass test tube (diameter 3.5 cm) for supporting a plant. Next, a plant, *Hippeastrum equestre*, was placed in the test tube, and 30 mL of the medium prepared by the above "2.1.2" of "A. Materials" was added to the test tube. After that, the plant is cultured for performing acclimation of the plant. After 7 days of acclimation, experiments on the thermal treatment and electrical stimulation were performed on the plant.

3.1 Thermal Treatment

After the acclimation, the test tube containing the plant and the medium (the original medium was kept, and not changed to a new medium) was directly placed in a 55° C. oven for the thermal treatment for 60 minutes. After that, the medium in the glass test tube was recovered in a 50 mL plastic centrifuge tube and frozen at −20° C. Next, the recovered medium was lyophilized to form a powder.

A liquid chromatography-mass spectrometry analysis was performed on the obtained powder to determine the content of galanthamine therein to investigate the effect of the thermal treatment only on a plant that produces galanthamine and releases it into the medium.

3.2 Combination of Thermal Treatment and Electrical Stimulation Treatment

After the acclimation, the test tube containing the plant and the medium (the original medium was kept, and not changed to a new medium) was directly placed in a 55° C. oven for thermal treatment for 60 minutes. Two platinum wire respectively used as a positive electrode and a negative electrode were passed through an upper cap and fixed thereon. After the thermal treatment, the upper cap having the positive electrode and the negative electrode was covered on the opening of the test tube containing the plant and medium (the original medium was kept, and not changed to a new medium) to let the positive electrode and the negative electrode enter the test tube and close the upper cap and the opening. It was noted that the positive electrode and the negative electrode could not contact each other inside the test tube, and the ends of the two electrodes had to be placed on both sides of the bulb of the plant (refer to FIG. 2). After that, an intermittent electrical stimulation was performed on the plant, i.e. the plant was electrified in an intermittent way. Specifically, after 1 minute of electrifying, electrifying was stopped for 1 minute, and then the electrification and the interruption of the electrification mentioned above were repeated to avoid a violent rise in temperature due to the thermoelectric effect. After repeating the foregoing pattern of electrification 10 times, the medium in the glass test tube was recovered in a 50 mL plastic centrifuge tube and frozen at −20° C. After that, the recovered medium was lyophilized to form a powder.

A liquid chromatography-mass spectrometry analysis was performed on the obtained powder to determine the content of galanthamine therein to investigate the effect of the thermal treatment plus the electrical stimulation treatment on a plant that produces galanthamine and releases it into the medium.

Results

The amounts of galanthamine released into the medium from the plant, *Hippeastrum equestre*, only subjected to the thermal treatment and the plant, *Hippeastrum equestre*, subjected to a combination of the thermal treatment and the electrical stimulation treatment are shown in Table 1.

TABLE 1

Amounts of galanthamine released into the medium from the plant, *Hippeastrum equestre*, only subjected to the thermal treatment and the plant, *Hippeastrum equestre*, subjected to a combination of the thermal treatment and the electrical stimulation treatment

|  | Thermal treatment | Combination of thermal treatment and electrical stimulation treatment |
|---|---|---|
| Galanthamine content in the medium (ppb) | — | 0.76 |

—: Lower than the detection line

Table 1 shows that the amount of galanthamine released into the medium from the plant, *Hippeastrum equestre*, subjected to a combination of the thermal treatment and the electrical stimulation treatment is greater than that of the plant, *Hippeastrum equestre*, only subjected to the thermal treatment.

4. Comparative Example 1

Galanthamine release of plants subjected to electrical stimulation treatment and none-electrical stimulation treatment after acclimation Methods 4.1 Acclimation of Plant The filter paper was cut and then placed at the bottom of a round glass test tube (diameter 3.5 cm) for supporting a plant. Next, a plant, *Lycoris aurea*, was placed in the test tube, and 30 mL of the medium prepared by the above "2.1.2" of "A. Materials" was added to the test tube. After that, the plant is cultured for performing acclimation of the plant. After 7 days of acclimation, experiments on the electrical stimulation treatment and none-electrical stimulation treatment were performed on the plants.

4.2 None-Electrical Stimulation Treatment

After the acclimation was completed, the medium in the test tube was recovered in a 50 mL plastic centrifuge tube and frozen at −20° C. on the same day. Next, the recovered medium was lyophilized to form a powder.

A liquid chromatography-mass spectrometry analysis was performed on the obtained powder to determine the content of galanthamine therein to investigate the effect of the acclimation on the plant that produces galanthamine and releases it into the medium.

4.3 Electrical Stimulation Treatment (Performing No Thermal Treatment)

Two platinum wire respectively used as a positive electrode and a negative electrode were passed through an upper cap and fixed thereon. After acclimation, the upper cap having the positive electrode and the negative electrode was covered on the opening of the test tube containing the plant and medium (the original medium was kept, and not changed to a new medium) to let the positive electrode and the negative electrode enter the test tube and close the upper cap and the opening. It was noted that the positive electrode and the negative electrode could not contact each other inside the test tube, and the ends of the two electrodes had to be placed on both sides of the bulb of the plant (refer to FIG. 2). After that, an intermittent electrical stimulation was performed on the plant, i.e. the plant was electrified in an intermittent way. Specifically, after 1 minute of electrifying, electrifying was stopped for 1 minute, and then the electrification and the interruption of the electrification mentioned above were repeated to avoid a violent rise in temperature due to the thermoelectric effect. After repeating the foregoing pattern of electrification 10 times, the medium in the glass test tube was recovered in a 50 mL plastic centrifuge tube and frozen at −20° C. After that, the recovered medium was lyophilized to form a powder.

A liquid chromatography-mass spectrometry analysis was performed on the obtained powder to determine the content of galanthamine therein to investigate the effect of directly performing the electrical stimulation treatment without thermal treatment after the acclimation on the plant that produces galanthamine and releases it into the medium.

4.4 The plants subjected to steps 4.2 and 4.3 were continuously cultured with a new medium in test tubes and, and after 7 days, the treatments of steps 4.2 and 4.3 were respectively performed on the same plants to determine the galanthamine-release amounts for the plants mentioned above on Day 7 of the experiments.

4.5 The treatment of the step 4.4 was repeated to determine the galanthamine-release amounts for the plants mentioned above on Day 14 of the experiments.

Results

Figure 6:
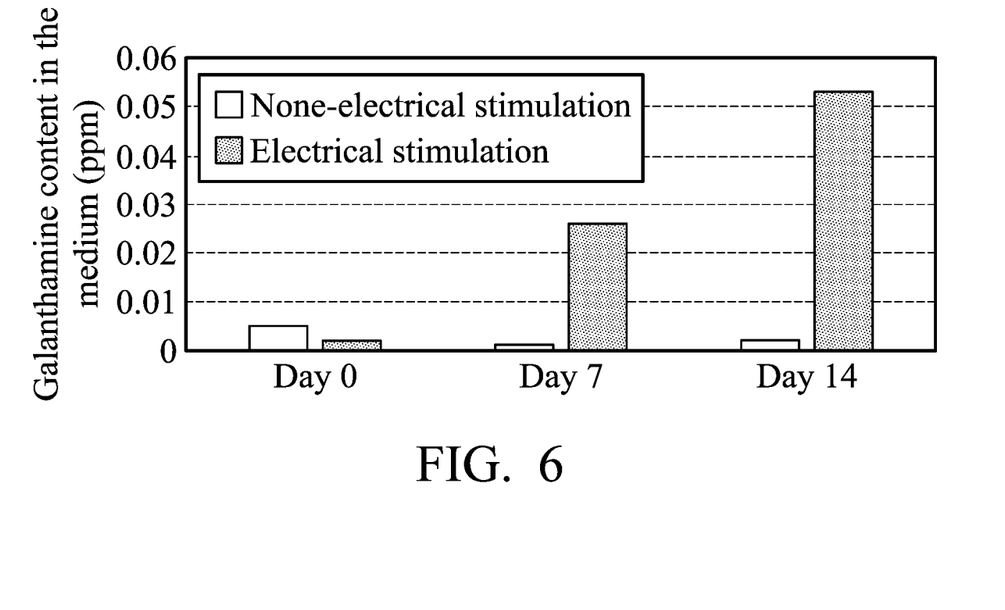
FIG. 6 shows the amounts of galanthamine released into the medium from the plant without the electrical stimulation treatment and the plant only subjected to the electrical stimulation treatment in one comparative example. Day 0: the day on which the acclimation is completed.

The amounts of galanthamine released into the medium from the plant that was only placed in a medium for performing the acclimation without the electrical stimulation treatment and the plant that, after the acclimation, was only subjected to the electrical stimulation treatment are shown in FIG. 6.

FIG. 6 shows that on Day 7 and Day 14 of the experiments, the amounts of galanthamine released into the medium from the plant subjected to the electrical stimulation treatment are all greater than those of the plant without the electrical stimulation treatment.

However, according to the results shown in FIG. 5 and FIG. 6, it is known that the amounts of galanthamine released into the medium from the plant subjected to the thermal treatment plus the electrical stimulation treatment is much greater than those of the plant only subjected to the electrical stimulation treatment.

5. Comparative Example 2

Galanthamine release of plants subjected to chemical inducer treatment
Methods

MS mediums containing chemical inducers (chitin (CA), salicylic acid (SA) and methyl jasmonate (MJ)) (final concentration of the chemical inducer is 25 μM) were prepared. Since the chemical inducers could not be high-strength autoclaved, after the preparations of the chemical inducers at room temperature were completed, sterilization by filtration was performed on the chemical inducers in a laminar flow. In the blank group, the medium contained no agent.

Healthy plants of *Lycoris aurea* with leaves and root with a bulb diameter of 0.6-0.8 cm were selected and withered epidermis on the bulb thereof was removed. The plant mentioned above was placed in a test tube having MS medium containing a chemical inducer and cultured under an illumination of 3000-4000 Lux with illumination time 16 hours an dark time 8 hours at an ambient temperature of 25-27° C.

30 mL of medium was recovered on the Day 0, Day 3, Day 7, Day 14, Day 28 and Day 35 of the culturing. The recovered medium was lyophilized to form a powder. A liquid chromatography-mass spectrometry analysis was performed on the obtained powder to determine the content of galanthamine therein to investigate the effect of the chemical stimulation treatment mentioned above on the plant that produces galanthamine and releases it into the medium.
Results
Results are shown in Table 2 and FIG. 7.

TABLE 2

Amounts of galanthamine released into the medium from the plants of *Lycoris aurea* only subjected to the chemical stimulation treatment

| Chemical inducer (ppm) | Day 0 | Day 3 | Day 7 | Day 14 | Day 28 | Day 35 |
|---|---|---|---|---|---|---|
| Chitin | 0 | 0.0015 | 0.0001 | 0.74 | — | — |
| Methyl jasmonate | 0 | 0.0153 | 0.0312 | 0.0066 | 2.72 | 0.9 |
| Salicylic acid | 0 | 0.0183 | 0.0077 | 0.0142 | 0.36 | 1.01 |
| Blank group | 0 | 0.0038 | 0.0355 | 2.06 | 0.21 | 1.25 |

—: Not detected

Figure 7:
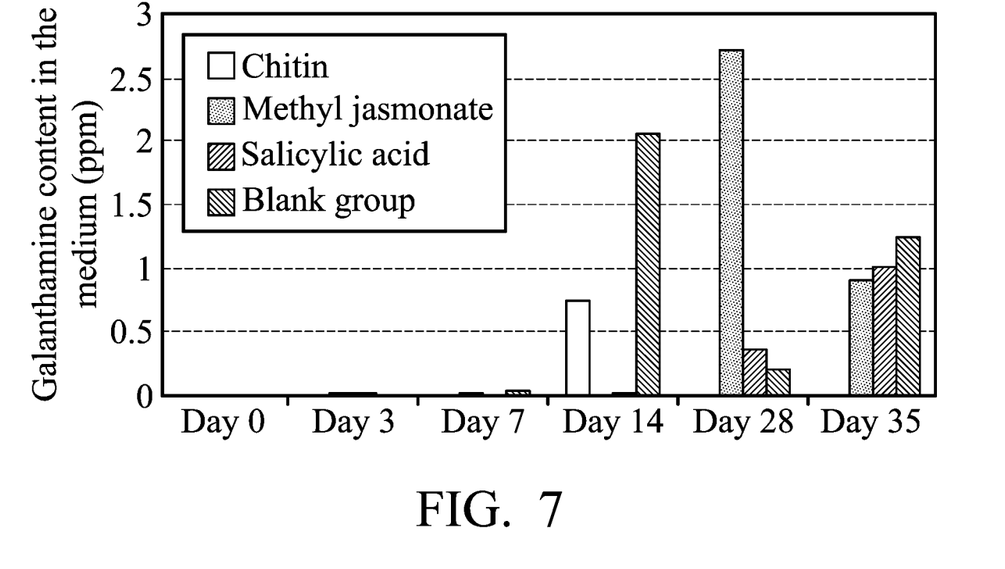
FIG. 7 shows the amounts of galanthamine released into the medium from plants subjected to different chemical inducers in one comparative example.

Table 2 and FIG. 7 show that methyl jasmonate has the best effect on production and release of galanthamine for the plant.

However, according to the results shown in FIG. 5 and FIG. 7, it is known that the amounts of galanthamine released into the medium from the plant subjected to the thermal treatment plus the electrical stimulation treatment is much greater than those of the plant only subjected to the chemical stimulation treatment.

Based on the integration of the foregoing experimental results, it is clearly known that as compared to the plant only subjected to the thermal treatment, the plant only subjected to the electrical stimulation treatment or the plant only subjected to the chemical stimulation treatment, the plant subjected to the thermal treatment plus the electrical stimulation treatment can produce and release larger amounts of galanthamine, and thus it is clearly known that a combination of thermal treatment and electrical stimulation treatment has an excellent synergistic effect for the process of producing galanthamine using a plant.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for producing galanthamine using a plant, comprising:
   (a) performing a thermal treatment on a whole living plant or a part of a whole living plant which remains in the whole living plant to induce accumulation of galanthamine therein, wherein the whole living plant is a plant belonging to the family Amaryllidaceae, and wherein the temperature of the thermal treatment is 40° C. to 60° C.;
   (b) placing the treated whole living plant or the whole living plant comprising the treated part in a medium for electrical stimulation treatment and performing an electrical stimulation treatment on the whole living plant to release the galanthamine from the whole living plant into the medium, wherein a voltage applied by the electrical stimulation is 3 V to 40 V and time required for the electrical stimulation treatment is 1 minute to 30 minutes; and
   (c) placing the treated whole living plant or the whole living plant comprising the treated part in a repair medium to repair the whole living plant after step (b).

2. The method for producing galanthamine using a plant as claimed in claim 1, wherein the plant belonging to the family Amaryllidaceae comprise a plant belonging to the genus *Lycoris*, a plant belonging to the genus *Hippeastrum* or a plant belonging to the genus *Narcissus*.

3. The method for producing galanthamine using a plant as claimed in claim 2, wherein the plant belonging to the genus *Lycoris* comprises *Lycoris aurea*, *Lycoris flavescens*, *Lycoris haywardii* or *Lycoris radiata*.

4. The method for producing galanthamine using a plant as claimed in claim 2, wherein the plant belonging to the genus *Hippeastrum* comprises *Hippeastrum equestre*, *Hippeastrum hybridum*, *Hippeastrum reginae*, *Hippeastrum brasiliense* or *Hippeastrum reticulatum*.

5. The method for producing galanthamine using a plant as claimed in claim 2, wherein the plant belonging to the genus *Narcissus* comprises *Narcissus tazetta*, *Narcissus jonquilla* or *Narcissus pseudonarcissus*.

6. The method for producing galanthamine using a plant as claimed in claim 1, wherein the time required for the thermal treatment is about 30-120 minutes.

7. The method for producing galanthamine using a plant as claimed in claim 1, wherein the thermal treatment comprises oven heating, double boiling, electric heating, or microwave heating.

8. The method for producing galanthamine using a plant as claimed in claim 1, wherein in step (a), the whole living plant or the part of the whole living plant which remains in the whole living plant is placed in a liquid.

9. The method for producing galanthamine using a plant as claimed in claim 8, wherein the liquid is the medium for electrical stimulation treatment.

10. The method for producing galanthamine using a plant as claimed in claim 1, wherein the content of nitrogen, phosphorous and potassium in solid ingredients of the medium for electrical stimulation treatment is about 30-55 w/w %.

11. The method for producing galanthamine using a plant as claimed in claim 1, wherein electrical conductivity of the medium for electrical stimulation treatment is about 1500-2000 μS/cm.

12. The method for producing galanthamine using a plant as claimed in claim 1, wherein a pH value of the medium for electrical stimulation treatment is about pH 5-7.

13. The method for producing galanthamine using a plant as claimed in claim 1, wherein the electrical stimulation treatment comprises an intermittent electrical stimulation.

14. The method for producing galanthamine using a plant as claimed in claim 13, wherein the intermittent electrical stimulation is performed with a power-on time of about 0.1-300 seconds and a power-off time of about 0.1-300 seconds.

15. The method for producing galanthamine using a plant as claimed in claim 1, wherein in the electrical stimulation treatment, a positive electrode and a negative electrode are in contact with the medium for electrical stimulation treatment and are placed on both sides of the treated whole living plant or the whole living plant comprising the treated part to perform an electrical stimulation on the treated whole living plant or the whole living plant comprising the treated part.

16. The method for producing galanthamine using a plant as claimed in claim 15, wherein electrical conductivities of materials of the positive electrode and the negative electrode are about $1 \times 10^2$-$6 \times 10^5$ s/cm.

17. The method for producing galanthamine using a plant as claimed in claim 15, wherein the materials of the positive electrode and the negative electrode independently comprise platinum, graphite, silver or gold.

18. The method for producing galanthamine using a plant as claimed in claim 1, further comprising (a') performing acclimation on the whole living plant prior to step (a).

19. The method for producing galanthamine using a plant as claimed in claim 18, wherein the time required for the acclimation is about 0.5-14 days.

20. The method for producing galanthamine using a plant as claimed in claim 18, wherein the acclimation comprises culturing the whole living plant in an acclimation medium.

21. The method for producing galanthamine using a plant as claimed in claim 1, wherein the treated whole living plant or the whole living plant comprising the treated part is placed in the repair medium for between 2 hours and 7 days.

22. The method for producing galanthamine using a plant as claimed in claim 1, further comprising (d) repeating steps (a)-(c) on the treated whole living plant or the whole living plant comprising the treated part after step (c).

23. The method for producing galanthamine using a plant as claimed in claim 1, further comprising (c') collecting galanthamine from the medium for electrical stimulation treatment after step (b).

* * * * *